US00PP18438P2

(12) United States Plant Patent
Kolster

(10) Patent No.: US PP18,438 P2
(45) Date of Patent: Jan. 15, 2008

(54) ***HYDRANGEA* PLANT NAMED 'KOLMAGIMO'**

(50) Latin Name: *Hydrangea paniculata*
Varietal Denomination: Kolmagimo

(75) Inventor: Peter R. Kolster, Boskoop (NL)

(73) Assignee: Kolster Beheer B.V., Boskoop (NL)

( * ) Notice: Subject to any disclaimer, the term of this patent is extended or adjusted under 35 U.S.C. 154(b) by 0 days.

(21) Appl. No.: 11/499,810

(22) Filed: Aug. 5, 2006

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Hydrangea* plant named 'Kolmagimo', characterized by its upright plant habit; strong and long flowering stems; and large inflorescences with greenish white-colored flowers.

3 Drawing Sheets

Botanical designation: *Hydrangea paniculata.*
Cultivar denomination: 'Kolmagimo'.

BACKGROUND OF THE INVENTION

The present invention relates to a new and distinct cultivar of *Hydrangea,* botanically known as *Hydrangea paniculata,* commercially used as a cut flower and hereinafter referred to by the name 'Kolmagimo'.

The objective of the breeding program is to create new *Hydrangea* cultivars with large inflorescences and strong flowering stems. The new *Hydrangea* originated from a cross-pollination made by the Inventor in 1999 in Boskoop, The Netherlands of two unnamed selections of *Hydrangea paniculata,* not patented. The new *Hydrangea* was discovered and selected by the Inventor as a single flowering plant within the progeny of the stated cross-pollination in a controlled environment in Boskoop, The Netherlands in 2001.

Asexual reproduction of the new *Hydrangea* by cuttings in a controlled environment in Boskoop, The Netherlands since June, 2002, has shown that the unique features of this new *Hydrangea* are stable and reproduced true to type in successive generations.

SUMMARY OF THE INVENTION

The cultivar 'Kolmagimo' has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Kolmagnmo'. These characteristics in combination distinguish 'Kolmagimo' as a new and distinct cultivar of *Hydrangea:*

1. Upright plant habit.
2. Strong and long flowering stems.
3. Large inflorescences with greenish white-colored flowers.

Plants of the new *Hydrangea* differ from plants of the parent selections primarily in flower form and size.

Plants of the new *Hydrangea* can be compared to plants of the cultivar Grandiflora, not patented. Plants of the new *Hydrangea* differ from plants of the cultivar Grandiflora in the following characteristics:

1. Plants of the new *Hydrangea* are larger than plants of the cultivar Grandiflora.
2. Plants of the new *Hydrangea* have stronger flowering stems than plants of the cultivar Grandiflora.
3. Plants of the new *Hydrangea* have larger flowers than plants of the cultivar Grandiflora.
4. Plants of the new *Hydrangea* and the cultivar Grandiflora differ in flower color as plants of the cultivar Grandiflora have white-colored flowers.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea.*

The photograph on the first sheet comprises a side perspective view of typical plants of 'Kolmagimo' grown in an outdoor nursery.

The photograph on the second sheet is a close-up view of a typical inflorescence of 'Kolmagimo'.

The photograph on the third sheet is a close-up view of a typical leaf of 'Kolmagimo'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and in the following description were grown in Boskoop, The Netherlands, in an outdoor nursery and under conditions which closely approximate commercial production conditions. During the production of the plants, day temperatures ranged from 15° C. to 32° C. and night temperatures ranged from 7° C. to 17° C. Plants of the new

*Hydrangea* were about two years old when the photographs and description were taken.

Botanical description: *Hydrangea paniculata* cultivar 'Kolmagimo'.

Parentage:

*Female, or seed, parent.*—Unnamed selection of *Hydrangea paniculata,* not patented.

*Male, or pollen, parent.*—Unnamed selection of *Hydrangea paniculata,* not patented.

Propagation:

*Type cutting.*—By cuttings.

*Time to initiate roots, summer.*—About 25 days at temperatures of 15° C. to 25° C.

*Time to initiate roots, winter.*—About 35 days at temperatures of 15° C. to 20° C.

*Time to produce a rooted young plant, summer.*—About 90 days at temperatures of 15° C. to 25° C.

*Time to produce a rooted young plant, winter.*—About 140 days at temperatures of 15° C. to 25° C.

*Root description.*—Fleshy; white in color.

*Rooting habit.*—Freely branching; moderately dense.

Plant description:

*Form/growth habit.*—Upright and broad plant habit; broad inverted triangle. Strong lateral branches; moderately vigorous growth habit.

*Plant height.*—About 106 cm.

*Plant diameter or area of spread.*—About 77 cm.

*Branching habit.*—Freely basal branching habit with about six lateral branches per plant.

*Lateral branches.*—Length: About 78 cm. Diameter: About 9 mm. Internode length: About 5.8 cm. Texture: Smooth, glabrous. Strength: Strong. Color: Young, 187B to 187C; older, 200D. Lenticels: Density: About eight per square centimeter. Length: About 1 mm. Width: About 0.75 mm. Color: 199D.

Foliage description:

*Arrangement.*—Opposite or in whorls of three, simple.

*Length.*—About 11.5 cm.

*Width.*—About 7.1 cm.

*Shape.*—Broadly ovate.

*Apex.*—Apiculate.

*Base.*—Rounded.

*Margin.*—Serrate.

*Texture, upper and lower surfaces.*—Rough; sparsely pubescent.

*Venation pattern.*—Pinnate.

*Color.*—Developing foliage, upper surface: Between 141A and 143A. Developing foliage, lower surface: 138B. Fully expanded foliage, upper surface: Slightly darker than 137A; venation, 143C. Fully expanded foliage, lower surface: 138A to 138B; venation, 144D.

*Petiole.*—Length: About 1.5 cm. Diameter: About 3 mm. Texture, upper and lower surfaces: Smooth, glabrous. Color, upper and lower surfaces: 146A to 146B.

Flower description:

*Flower type and habit.*—Single rotate flowers arranged on large terminal compound panicles. Flowers face upright to outward. Flowers persistent.

*Fragrance.*—Faint.

*Natural flowering season.*—Continuous flowering during the summer in The Netherlands.

*Flower longevity.*—Flowers last about four weeks on the plant and about ten days as a cut flower.

*Quantity of flowers.*—Freely flowering; about 2,500 fertile flowers and about 650 sterile flowers per panicle.

*Panicle height.*—About 28 cm.

*Panicle diameter.*—About 27.3 cm.

*Flower diameter, fertile flowers.*—About 9 mm.

*Flower diameter, sterile flowers.*—About 2.8 cm.

*Flower depth (height), fertile flowers.*—About 9 mm.

*Flower depth (height), sterile flowers.*—About 4 mm.

*Flower buds, fertile and sterile flowers.*—Length: About 2 mm. Diameter: About 1.5 mm. Shape: Obovate. Color: 145D.

*Petals, fertile flowers only.*—Arrangement: Four in a single whorl. Length: About 3 mm. Width: About 1.5 mm. Shape: Ovate. Apex: Acute. Base: Attenuate. Margin: Entire. Texture, upper and lower surfaces: Smooth, glabrous. Color: When opening and fully opened, upper surface: 157C to 157D. When opening and fully opened, lower surface: 157C to 157D.

*Sepals, fertile flowers.*—Quantity per flower: Five in a single whorl; fused at base. Length: About 1 mm. Width: About 1 mm. Shape: Deltoid. Apex: Acute. Base: Broadly cuneate. Margin: Entire. Texture, upper and lower surfaces: Smooth, glabrous. Color: When opening, upper and lower surfaces: 145C. Fully opened, upper and lower surfaces: 145B.

*Sepals, sterile flowers.*—Quantity per flower: Four in a single whorl. Length: About 1.4 cm. Width: About 1.4 cm. Shape: Orbicular to broadly elliptical. Apex: Obtuse. Base: Cuneate. Margin: Entire. Texture, upper and lower surfaces: Smooth, glabrous. Color: When opening, upper surface: 145C. When opening, lower surface: 145C to 145D. Fully opened, upper and lower surfaces: 157D; color becoming closer to 143C with development.

*Peduncles.*—Angle: Erect. Strength: Strong. Length: About 25.5 cm. Diameter: About 4 mm. Color: 145B; towards the base, 183D.

*Pedicels, fertile flowers.*—Angle: About 10° from vertical. Strength: Strong. Length: About 3 mm. Diameter: About 0.5 mm. Color: 145D.

*Pedicels, sterile flowers.*—Angle: About 45° from vertical. Strength: Strong. Length: About 1.6 cm. Diameter: About 1 mm. Color: 145D.

*Reproductive organs, fertile flowers only.*—Stamens: Quantity per flower: About eleven. Filament length: About 3 mm. Filament color: 157C to 157D. Anther shape: Broadly elliptical. Anther length: About 0.7 mm. Anther color: 198C. Pollen amount: Scarce. Pollen color: Lighter than 198C. Pistils: Pistil quantity per flower: About three. Pistil length: About 2 mm. Stigma shape: Club-shaped. Stigma color: 145D. Style length: About 1 mm. Style color: 145D. Ovary color: 145B to 145C.

*Seed/fruit.*—Seed and fruit development has not been observed.

Disease/pest resistance: Under commercial production conditions, plants of the new *Hydrangea* have not been observed to be resistant to pathogens or pests common to *Hydrangea.*

Temperature tolerance: Plants of the new *Hydrangea* have been shown to be tolerant to temperatures ranging from about −30° C. to about 37° C.

It is claimed:

1. A new and distinct *Hydrangea* plant named 'Kolmagimo' as illustrated and described.

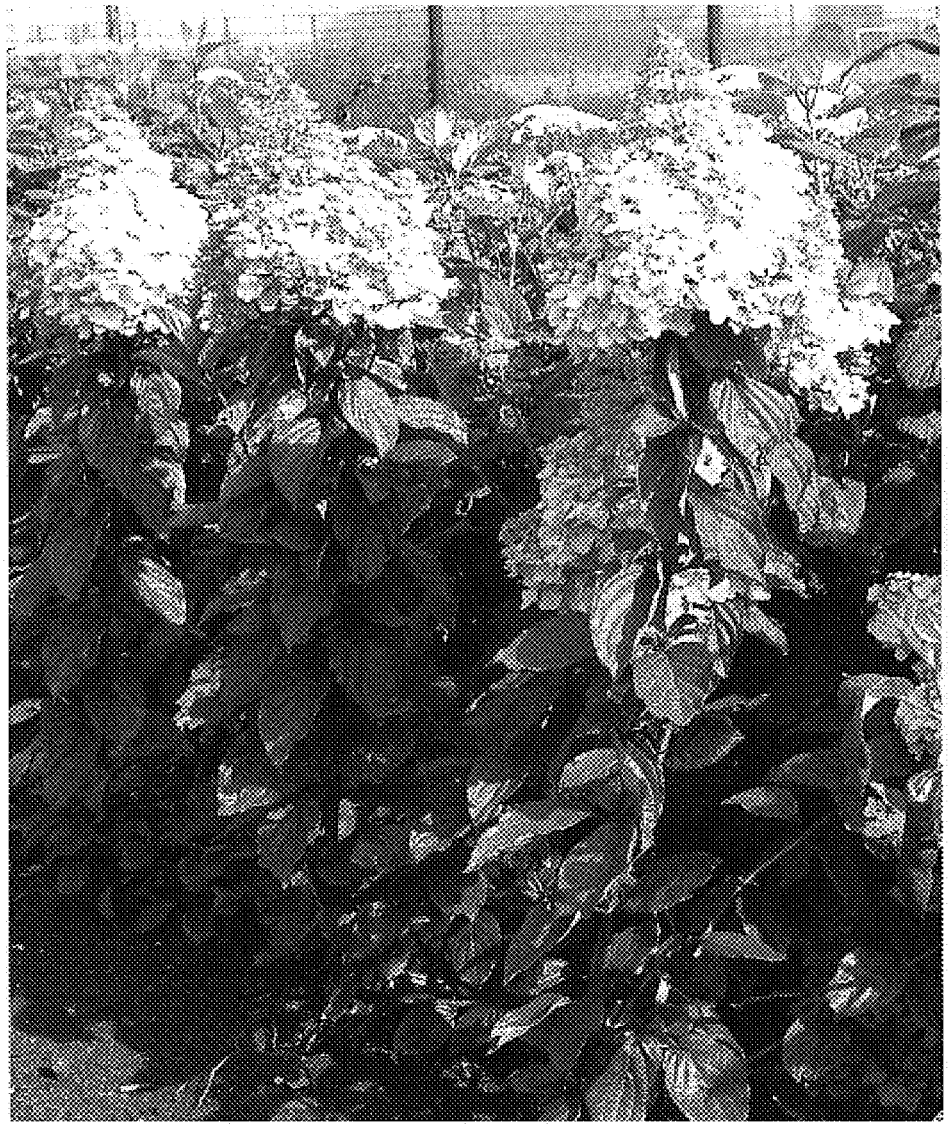

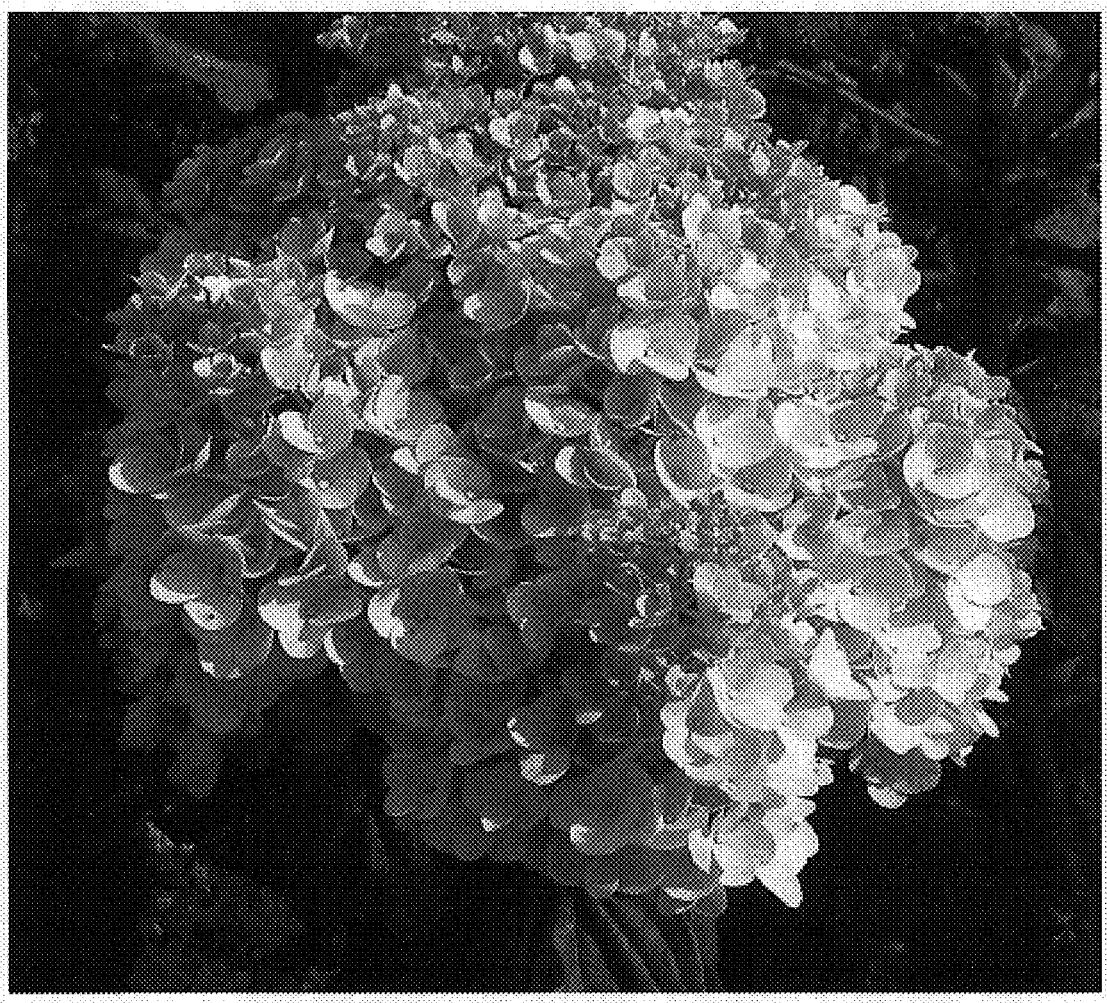

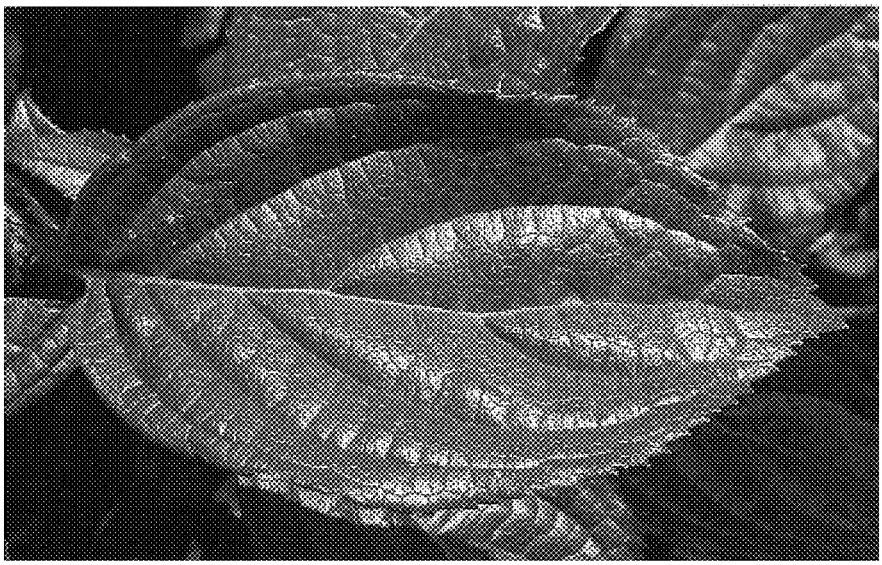

* * * * *